United States Patent [19]

Holtkamp, Sr.

[11] Patent Number: Plant 6,549

[45] Date of Patent: Jan. 24, 1989

[54] AFRICAN VIOLET PLANT NAMED LANAI

[75] Inventor: Reinhold Holtkamp, Sr., Isselburg, Fed. Rep. of Germany

[73] Assignee: Gessellschaftsvertrag uber die Erfindergemeinschaft "Optimara", Rees Haffen, Fed. Rep. of Germany

[21] Appl. No.: 56,146

[22] Filed: Jun. 1, 1987

[51] Int. Cl.[4] ..... A01H 5/00

[52] U.S. Cl. ..... Plt./69

[58] Field of Search ..... Plt. 69

*Primary Examiner*—James R. Feyrer

*Attorney, Agent, or Firm*—Foley & Lardner, Schwartz, Jeffery, Schwaab, Mack, Blumenthal & Evans

[57] ABSTRACT

An African violet plant named Lanai, characterized by its single violet-shaped purple flowers, occasionally semi-double, with fine white edge, slightly frilled; strong upright flower stems, forming a tight bouquet above the leaves; profuse flowering; vigorous growth habit; medium green, serrated, spear-shaped leaves; and long lasting and non-dropping flowering habit.

1 Drawing Sheet

The present invention comprises a new and distinct cultivar of African violet plant, botanically known as *Saintpaulia ionantha,* and hereinafter referred to by the cultivar name Lanai.

The new cultivar was referred to during the breeding and selection process by the designation H72/2, and is a product of a planned breeding program. The new cultivar was originated from a cross made by applicant in a controlled breeding program in Haffen, Federal Republic of Germany. The female, or seed parent was a cultivar designated 87 and named Arizona, disclosed in U.S. Plant Pat. No. 4,374. The male, or pollen parent was a cultivar designated GG18.

Lanai was discovered and selected by me as a flowering plant within the progeny of the stated cross in a controlled environment in Haffen, Federal Republic of Germany. Asexual reproduction of the new cultivar by leaf cuttings, as performed by me at Haffen, Federal Republic of Germany, has demonstrated that the combination of characteristics as herein disclosed for the new cultivar are firmly fixed and retained through successive generations of asexual reproduction.

Lanai has not been observed under all possible environmental conditions. The phenotype may vary significantly with variations in environment such as temperature, light intensity and day length. The following observations, measurements and values describe the new cultivar as grown in 10 cm pots in Haffen, Federal Republic of Germany and Nashville, Tenn. under greenhouse conditions which closely approximate those generally used in commercial practice.

The following traits have been repeatedly observed and are determined to be basic characteristics of Lanai which in combination distinguish this African violet as a new and distinct cultivar:

1. Single violet-shaped purple flowers, occasionally semi-double, with fine white edge, slightly frilled.
2. First flash of flowers forms a tight bouquet above the leaves on strong upright flower stems.
3. After maturity, the flowers dry off and remain on the peduncle without becoming infected by botrytis.
4. Profuse flowering.
5. Each plant carries 8–10 and more upright flower stems of which each carries 7–9 and more flowers.
6. Vigorous grower.
7. Plant saleable 10–11 weeks after potting.

8. Medium green, serrated, spear-shaped leaves.
9. Long-lasting, non-dropping flowers.
10. Seed capsule pushes slightly through.

The accompanying color photographic drawing shows a typical specimen plant of the new cultivar. The colors appearing in the photograph are as true as possible with color illustration of this type.

In the following description, color references are made to The Royal Horticultural Society Color Chart (RHS), except where general colors of ordinary significance are referred to. Color values were taken under natural light conditions at approximately 2:00 p.m. in Nashville, Tenn. Under cooler growing conditions and more intensive lighting the purple color is going to be more intense.

Botanical classification: *Saintpaulia ionantha,* Ramat., cv. Lanai.

Parentage:

*Male parent.*—GG18.

*Female parent.*—87, named Arizona.

Propagation: The new cultivar holds its distinguishing characteristics through successive propagations by leaf cuttings and by division of shoots.

Plant: From 8–11 cm tall when grown in pots, and approximately 20–23 cm in diameter when fully grown. The growth rate is vigorous.

*Leaves.*—Shape: Spear-shaped. Diameter: 55–65 mm wide and 70–80 mm long. Texture: Velvety. Ribs and Veins: Upperside well visible and lighter than rest of leaf; underside very well pronounced, light green and shiny. Color (upper side): Green 137 between A and B. Color (under side): Light green veins; in between the veins the color is red purple. Petioles: Strong, upright, purplish green, hairy.

*Flowers.*—Buds: Bell-shaped, 8–10 mm before opening. Sepals: Five (5) in number, purplish-brown. Calyx: Funnel-shaped. Peduncle: Strong, upright, purplish brown, hairy.

*Individual flowers.*—Size: 35 to 40 mm in diameter. Shape: violet-shaped, single, occasionally semi-double. Color (upper side): Purple violet 81A with white margins. Color (under side): Purple violet 81B with white margins. Borne: Each flower stem carries 7–9 and more flowers on strong, upright, wirelike peduncles that are free standing above the leaves. Flowering habit: Flowers 9–10 weeks after potting.

*Reproductive organs.*—Stamens: 2. Anthers: 2 stamens composed of 4 anther cells, seed capsule pushes slightly through. Filaments: 5 mm long, yellowish green. Pollen Color: Yellow 7A. Styles: 7 mm purple.

*Roots.*—Normally developed, white when young, turning slightly brownish when older.

Disease resistance: Good.

General observations: Lanai is a vigorous grower with attractive medium green, spear-shaped, serrated leaves. Out of the center, 8–10 and more strong flower stems appear that are slightly bending toward the center, each carrying 7–9 and more purple, violet-shaped flowers, with frilled, white edges. The flowers are single, but occasionally they have 3 additional small petals that make them appear to be semi-double. Approximately 10–11 weeks after potting the plant is saleable. The flowers are long-lasting and non-dropping, and the seed capsule pushes through.

I claim:

1. A new and distinct cultivar of African violet named Lanai, as described and illustrated, and particularly characterized by its single violet-shaped purple flowers, occasionally semi-double, with fine white edge, slightly frilled; strong upright flower stems, forming a tight bouquet above the leaves; profuse flowering; vigorous growth habit; medium green, serrated, spear-shaped leaves; and long lasting and non-dropping flowering habit.

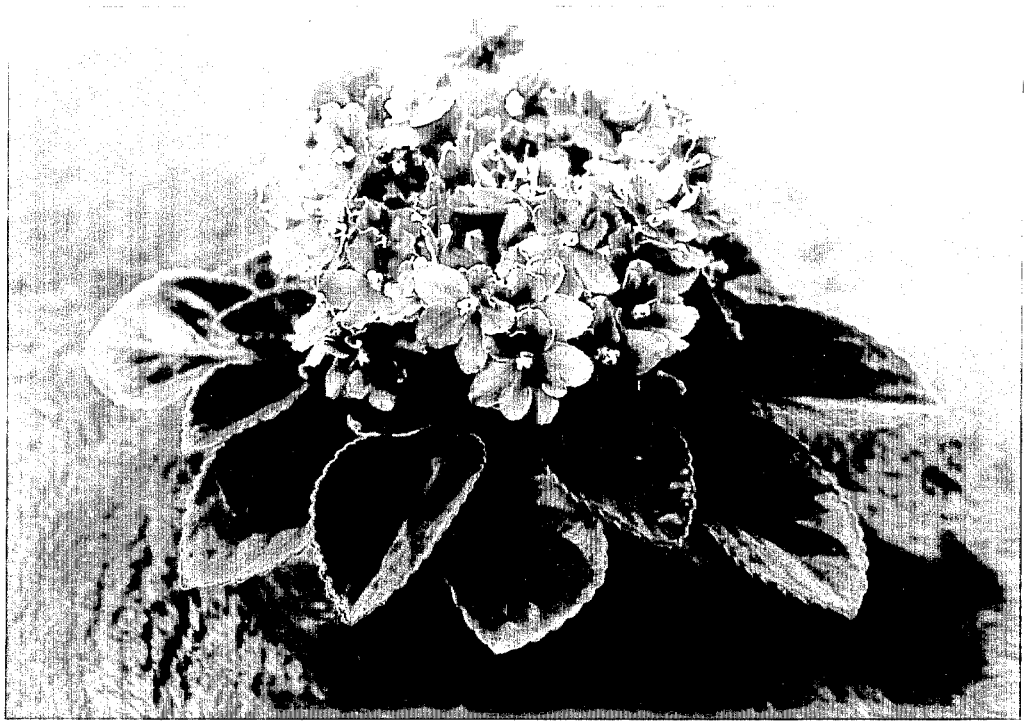

* * * * *